United States Patent
Kyushima et al.

(10) Patent No.: US 6,472,664 B1
(45) Date of Patent: Oct. 29, 2002

(54) PHOTOMULTIPLIER TUBE TIGHTLY ARRANGED WITH SUBSTANTIALLY NO SPACE BETWEEN ADJACENT TUBES

(75) Inventors: Hiroyuki Kyushima, Hamamatsu (JP); Akira Atsumi, Hamamatsu (JP); Hideki Shimoi, Hamamatu (JP); Tomoyuki Okada, Hamamatsu (JP); Masuo Ito, Hamamatsu (JP)

(73) Assignee: Hamamatsu-Photonics, Ltd., Hamamatsu (JP)

( * ) Notice: Subject to any disclaimer, the term of this patent is extended or adjusted under 35 U.S.C. 154(b) by 0 days.

(21) Appl. No.: 09/701,540
(22) PCT Filed: Jun. 1, 1999
(86) PCT No.: PCT/JP99/02921
§ 371 (c)(1), (2), (4) Date: Nov. 30, 2000
(87) PCT Pub. No.: WO99/63573
PCT Pub. Date: Dec. 9, 1999

(30) Foreign Application Priority Data

| Jun. 1, 1998 | (JP) | 10-151596 |
| Jun. 1, 1998 | (JP) | 10-151603 |
| Aug. 26, 1998 | (JP) | 10-240373 |

(51) Int. Cl.$^7$ ............................................. G01T 1/20
(52) U.S. Cl. .................. 250/366; 313/103 R; 313/532; 313/533
(58) Field of Search ......................... 250/366; 313/532, 313/533, 103 R

(56) References Cited

U.S. PATENT DOCUMENTS

| 3,919,556 A | * 11/1975 | Berninger | 250/363.07 |
| 5,077,504 A | * 12/1991 | Helvy | 313/103 R |
| 5,329,124 A | * 7/1994 | Yamamoto et al. | 250/366 |

FOREIGN PATENT DOCUMENTS

| JP | 5-36372 | 2/1993 | |
| JP | 5-281362 | 10/1993 | |
| JP | 09320511 A | * 12/1997 | H01J/43/04 |

* cited by examiner

Primary Examiner—Constantine Hannaher
(74) Attorney, Agent, or Firm—Oliff & Berridge, PLC

(57) ABSTRACT

A photomultiplier tube unit including photomultiplier tubes densely assembled and thereby having an improved light sensing efficiency. The outer surfaces (2b) of metal side tubes (2) of photomultiplier tubes (1) are in facial contact with one another, and thereby a high-density arrangement of photomultiplier tubes (1) are achieved. The side tubes (2) can be electrically connected to one another, and therefore the side tubes (2) can be easily made equipotential. As a result, it is unnecessary to electrically connect the stem pin (10) to the side tube (2) of each photomultiplier tube (1), facilitating the assembling of the photomultiplier tube unit. When a required photomultiplier tube (1) in a device (e.g., a gamma camera) having thus-united multiple photomultiplier tubes is replaced with a new one, the troublesome work of replacing photomultiplier tubes one by one is obviated, simplifying the replacement work.

9 Claims, 14 Drawing Sheets

PHOTOMULTIPLIER TUBE TIGHTLY ARRANGED WITH SUBSTANTIALLY NO SPACE BETWEEN ADJACENT TUBES

TECHNICAL FIELD

The present invention relates to a photomultiplier tube unit designed to detect through multiplication weak light radiated onto a faceplate. The present invention also relates to a radiation detector using this type of photomultiplier tube unit.

BACKGROUND ART

Conventional photomultiplier tubes are described in Japanese Unexamined Patent Application Publication Nos. HEI-5-290793 and HEI-9-306416. The photomultiplier tubes described therein include a metal side tube having a polygonal cross-section with a flange portion protruding laterally from the bottom of the tube. Similarly, the metal stem plate is provided with a flange portion that protrudes laterally. The flange portions of the side tube and stem plate overlap and are fused through resistance welding to form a hermetically sealed vessel. When using the photomultiplier tube thus constructed in a radiation detector (such as, gamma camera), a plurality of the photomultiplier tubes are arranged in a matrix formation within the detector while confronting the faceplate of each photomultiplier tube with the scintillator.

However, when a plurality of photomultiplier tubes are arranged two-dimensionally in the detector, the flange portions of the photomultiplier tubes interfere with the use of the tube. Arranging a plurality of photomultiplier tubes closely together will form dead spaces in the flange portions. As a result, a gap is formed between adjacent faceplates, causing light detection efficiency to lower.

DISCLOSURE OF THE INVENTION

The present invention has been made to solve the above-described problems, and accordingly it is an object of the present invention to provide a photomultiplier tube unit including a plurality of photomultiplier tubes densely assembled and thereby having an improved light sensing efficiency. Another object of the present invention is to provide a radiation detector with an improved performance.

The photomultiplier tube unit according to the present invention uses a plurality of photomultiplier tubes that are juxtaposed wherein each of the plurality of photomultiplier tube includes a faceplate, a photocathode for emitting electrons in response to light incident on the faceplate, an electron multiplying section, disposed inside an airtight vessel, for multiplying the electrons emitted from the photocathode, and an anode for outputting an output signal based on the electrons multiplied by the electron multiplying section. The airtight vessel includes: a metal stem plate for fixedly supporting the electron multiplying section and the anode with stem pins; a metal side tube with the stem plate fixed on one open end, and enclosing the electron multiplying section and the anode; and a faceplate fixed on the other open end of the metal side tube, wherein a plurality of airtight vessels are juxtaposed and outer surfaces of the plurality of airtight vessels are in facial contact with one another each outer surface being perpendicular in entirety to the corresponding photocathode.

Because the photomultiplier tube is constructed so that the outer surfaces of the metal side tubes are in facial contact with one another, wherein each outer surface is perpendicular in entirety to the corresponding photocathode, a high-density arrangement of the photomultiplier tubes can be achieved. Furthermore, the side tubes of the respective photomultiplier tubes can be electrically connected and the side tubes can be easily made equipotential. As a result, it is unnecessary to electrically connect the stem pin to the side tube of each photomultiplier tube, facilitating the assembly of the photomultiplier tube unit. When a required photomultiplier tube in a device (e.g., a gamma camera) having thus-united multiple photomultiplier tubes is replaced with a new one, the troublesome work of replacing photomultiplier tubes one by one is obviated, simplifying the replacement work.

It is preferable that the plurality of airtight vessels be arranged and fixed on a single substrate. The photomultiplier tubes are arranged on the substrate so that not only is it easy to align the photomultiplier tubes but the alignment accuracy is also improved. Moreover, the management of the number and the arrangement of the photomultiplier tubes in one unit can be performed depending on the shape of the substrate, so the maintenance and the management on a unit basis can be easily done.

It is also preferable that the substrate be formed with a plurality of pin holes for allowing the stem pins to be inserted therein. With the use of such a structure, the photomultiplier tubes can be accurately aligned on the substrate by a simple procedure such that the stem pins of each photomultiplier tube are inserted into the corresponding pin holes.

It is also preferable that the substrate be provided with a plurality of socket pins having an upper portion formed with a concave portion for allowing the stem pin to be inserted therein. With the use of such a structure, the photomultiplier tubes can be accurately aligned on the substrate by a simple procedure such that the stem pins of each photomultiplier tube are inserted into the corresponding concave portions of the socket pins.

It is preferable that the outer surfaces of the side tubes be in facial contact with one another via an electrically conductive adhesive. With the use of such a structure, the side tubes of the photomultiplier tubes can be fixed simply and accurately. Further, the side tubes can be electrically connected with accuracy. As such, the device of an anti-vibration structure can be provided.

According to another aspect of the present invention, there is provided a radiation detector including a scintillator for emitting fluorescent light in response to radiation generated from an object of analysis, a plurality of photomultiplier tubes, each having a faceplate disposed in opposition to the scintillator, for outputting electric charges based on fluorescent light emitted from the scintillator, and a position calculating section for performing calculations on the electric charges output from the plurality of photomultiplier tubes and outputting positioning signals of radiation issued from the object of analysis. Each of the plurality of the photomultiplier tubes includes: a faceplate; a photocathode for emitting electrons in response to light incident on the faceplate; an electron multiplying section, disposed inside an airtight vessel, for multiplying the electrons emitted from the photocathode; and an anode for outputting an output signal based on the electrons multiplied by the electron multiplying section. The airtight vessel includes: a metal stem plate for fixedly supporting the electron multiplying section and the anode with stem pins; a metal side tube with the stem plate fixed on one open end, and enclosing the electron multiplying section and the anode; and a faceplate fixed on the other open end of the metal side tube. The radiation detector includes a photomultiplier tube unit in which a plurality of airtight vessels are juxtaposed, and outer surfaces of the plurality of airtight vessels are in facial contact with one another each outer surface being perpendicular in entirety to the corresponding photocathode.

Because the photomultiplier tube unit for use in the radiation detector is constructed so that the outer surfaces of the metal side tubes are in facial contact with one another, wherein each outer surface is perpendicular in entirety to the corresponding photocathode 3a, a high-density arrangement of the photomultiplier tubes can be achieved. Furthermore, the side tubes of the respective photomultiplier tubes can be electrically connected and the side tubes can be easily made equipotential. As a result, it is unnecessary to electrically connect the stem pin to the side tube of each photomultiplier tube, facilitating the assembly of the photomultiplier tube unit. When a required photomultiplier tube in a device (e.g., a gamma camera) having thus-united multiple photomultiplier tubes is replaced with a new one, the troublesome work of replacing photomultiplier tubes one by one is obviated and the replacement work can be accomplished at a high speed. When the photomultiplier tube is disposed in such a manner that the faceplate is disposed in opposition to the scintillator, a high-density arrangement and easy assembly of the photomultiplier tubes can be achieved, thereby enhancing the property of the radiation detector.

It is preferable that the photomultiplier tube unit be such that a plurality of airtight vessels are arranged and fixed on a single substrate. With the use of such a structure, assembling and replacement of the photomultiplier tubes are performed on a substrate basis, reliability of the entire device is maintained. With the use of the substrate, the alignment accuracy can be improved. Moreover, the management of the number and the arrangement of the photomultiplier tubes in one unit can be performed depending on the shape of the substrate, so the maintenance and the management of the photomultiplier tube in the radiation detector can be easily done.

The photomultiplier tube unit according to the present invention is constructed as described above, an improved light sensing efficiency can be achieved with a high-density arrangement of the photomultiplier tubes. The radiation detector according to the present invention uses the above-described photomultiplier tube unit, so that performance of the radiation detector can be improved.

BEST MODE FOR CARRYING OUT THE INVENTION

A photomultiplier tube unit and a radiation detector according to preferred embodiments of the present invention will be described while referring to the accompanying drawings.

Figure 1:
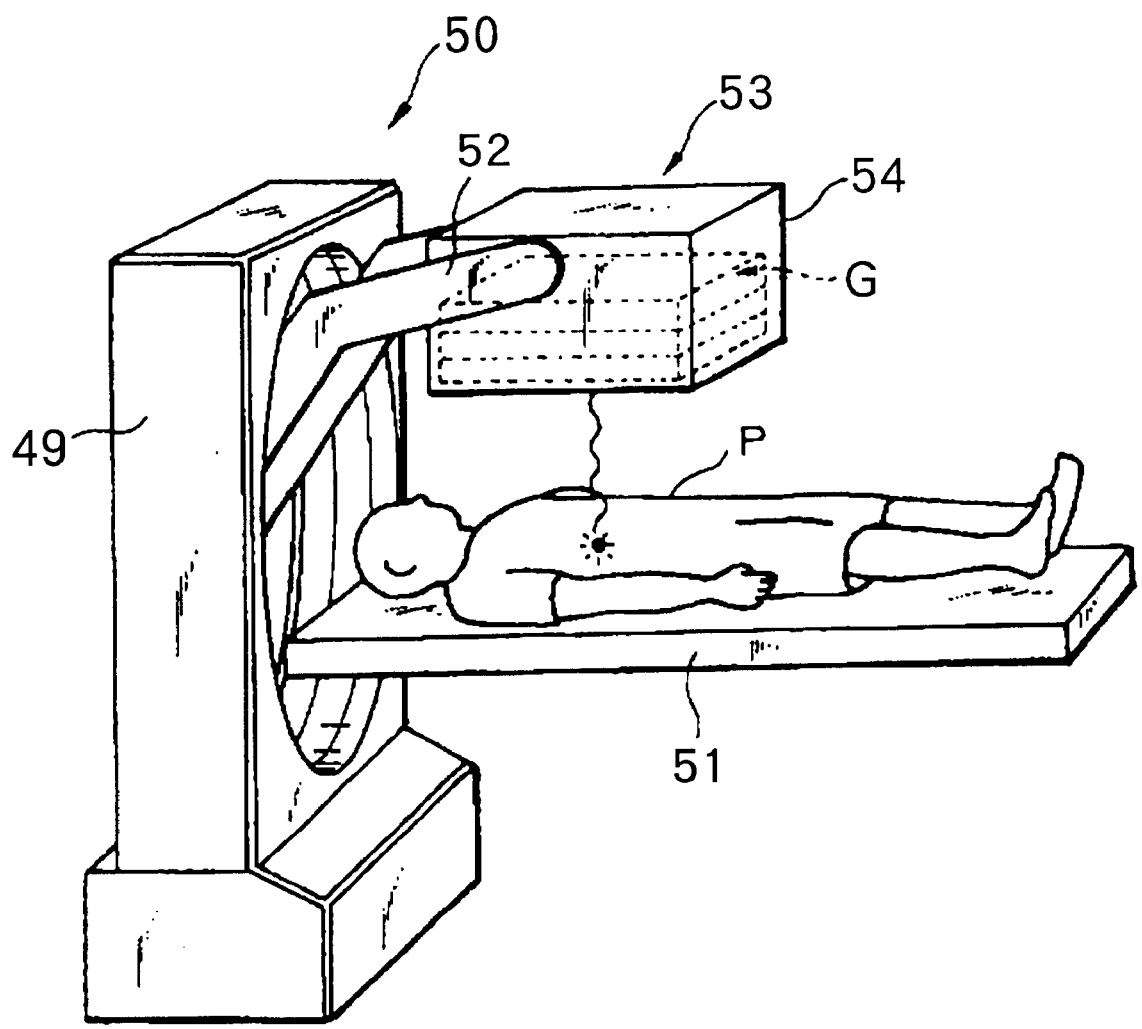
FIG. 1 is a perspective view showing a radiation detector according to an embodiment of the present invention.

FIG. 1 is a perspective view showing the radiation detector according to the present invention. As shown in FIG. 1, a gamma camera 50 serves as the radiation detector of the present example. The gamma camera 50 was developed in nuclear medicine as a diagnostic apparatus. The gamma camera 50 includes a support frame 49; arms 52 extending from the support frame 49; a detector 53 supported by the arms 52; and a bed 51 positioned directly underneath the detector 53 for supporting a prostrated patient to be examined.

Figure 2:
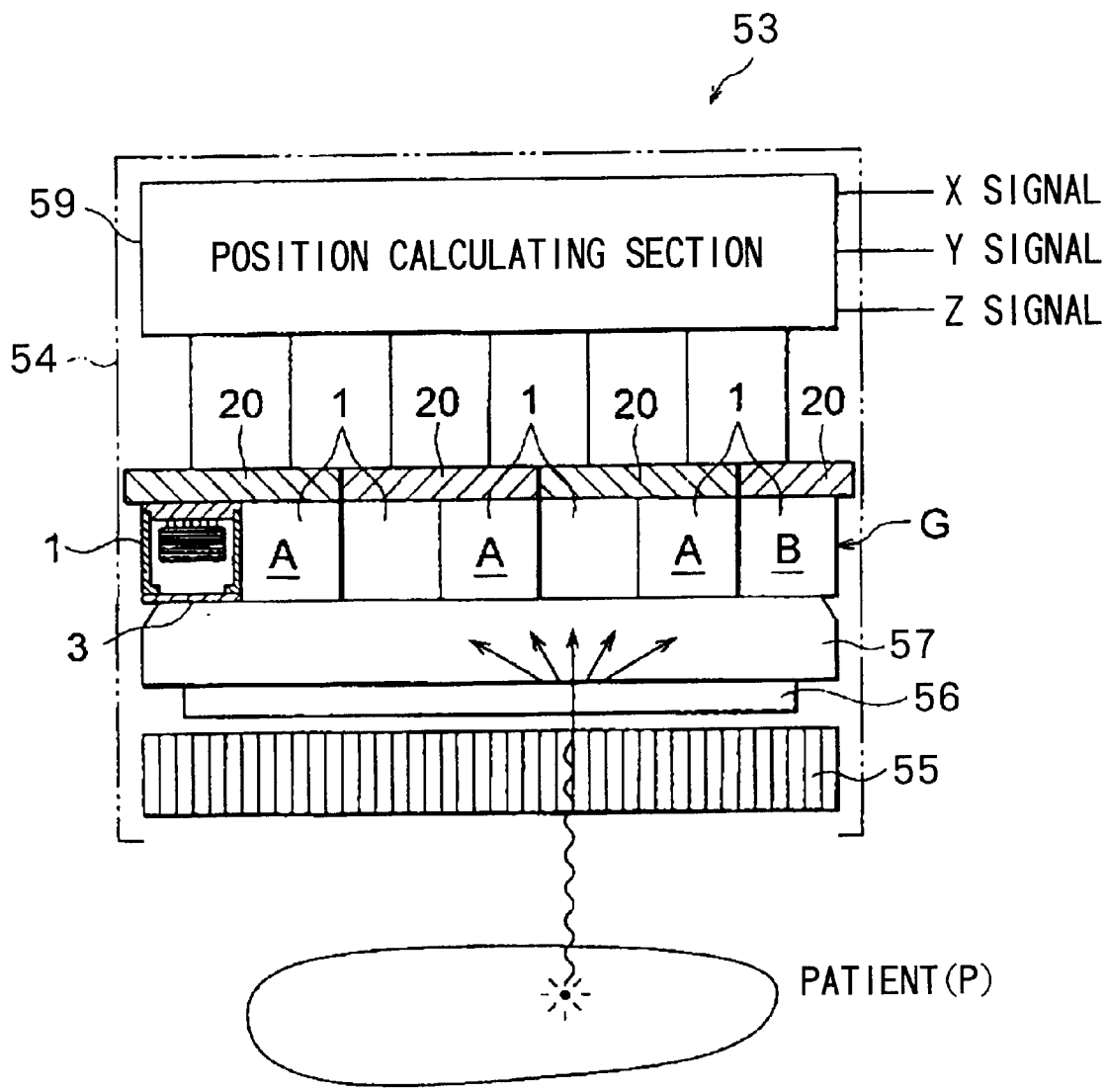
FIG. 2 is a side view showing the internal structure of the radiation detector.

As shown in FIG. 2, the detector 53 includes an outer casing 54; a collimator 55 provided at the bottom level of the outer casing 54 at a position opposing the diseased part of the patient; a scintillator 56 disposed above the collimator 55 in the outer casing 54; a group of photomultiplier tubes G; and a light guide 57 for fixing the scintillator 56 to the group of photomultiplier tubes G. The group of photomultiplier tubes A includes a plurality of the photomultiplier tubes 1 arranged in a densely packed matrix formation. The faceplates 3 of the photomultiplier tubes 1 face downward in opposition to the scintillator 56 since the scintillator 56 emit fluorescent light onto the faceplate 3 via the light guide 57.

A position calculating section 59 for computing processes based on output charges from each photomultiplier tube 1 is provided in the outer casing 54. The position calculating section 59 outputs an X signal, Y signal, and Z signal for creating a 3-dimensional image on a display monitor (not shown). The light guide 57 converts gamma rays generated from the diseased part of the patient into prescribed fluorescent light. Each of the photomultiplier tube 1 converts this fluorescent energy into electrical charges, after which the position calculating section 59 outputs the charges externally as position signals. In this way, the distribution of radiation energy can be displayed on the monitor for use in diagnoses.

In the brief example above, the gamma camera 50 is used as the radiation detector. However, another example of a radiation detector used in nuclear medicine diagnoses is a positron CT, known as a PET. It is obvious that a plurality of photomultiplier tube 1 according to the present invention can also be employed in this apparatus.

Figure 3:
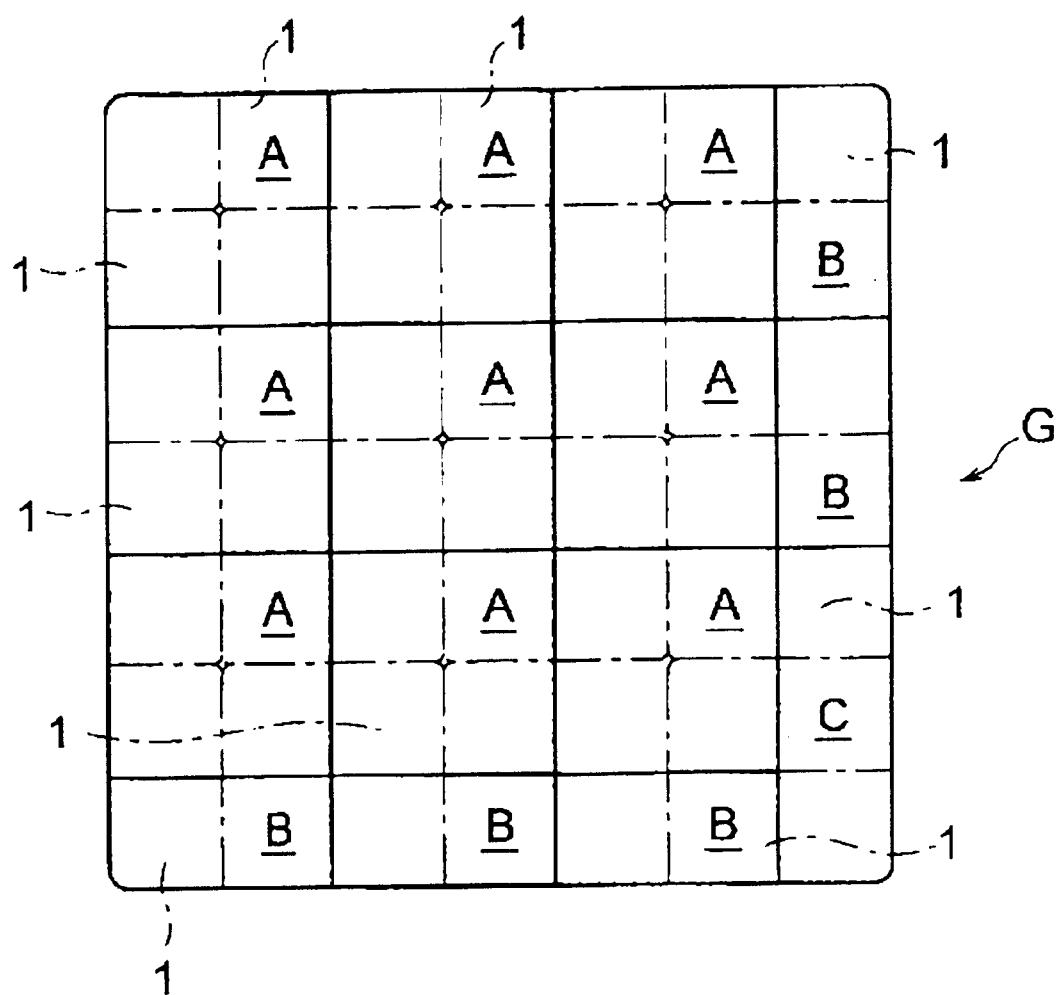
FIG. 3 is a plan view showing arrangement of the photomultiplier tubes.

The group of photomultiplier tubes G is attained by arranging photomultiplier tubes of the same configuration in a matrix formation. One example is shown in FIG. 3. The group of photomultiplier tubes G shown therein includes a photomultiplier tube unit A having four (2 by 2) photomultiplier tubes 1, a photomultiplier tube unit B having two (2 by 1) photomultiplier tubes 1, and a photomultiplier tube unit C having three (3 by 1) photomultiplier tubes 1.

Description will be given with respect to the photomultiplier tube unit A arranged in a matrix formation.

Figure 4:
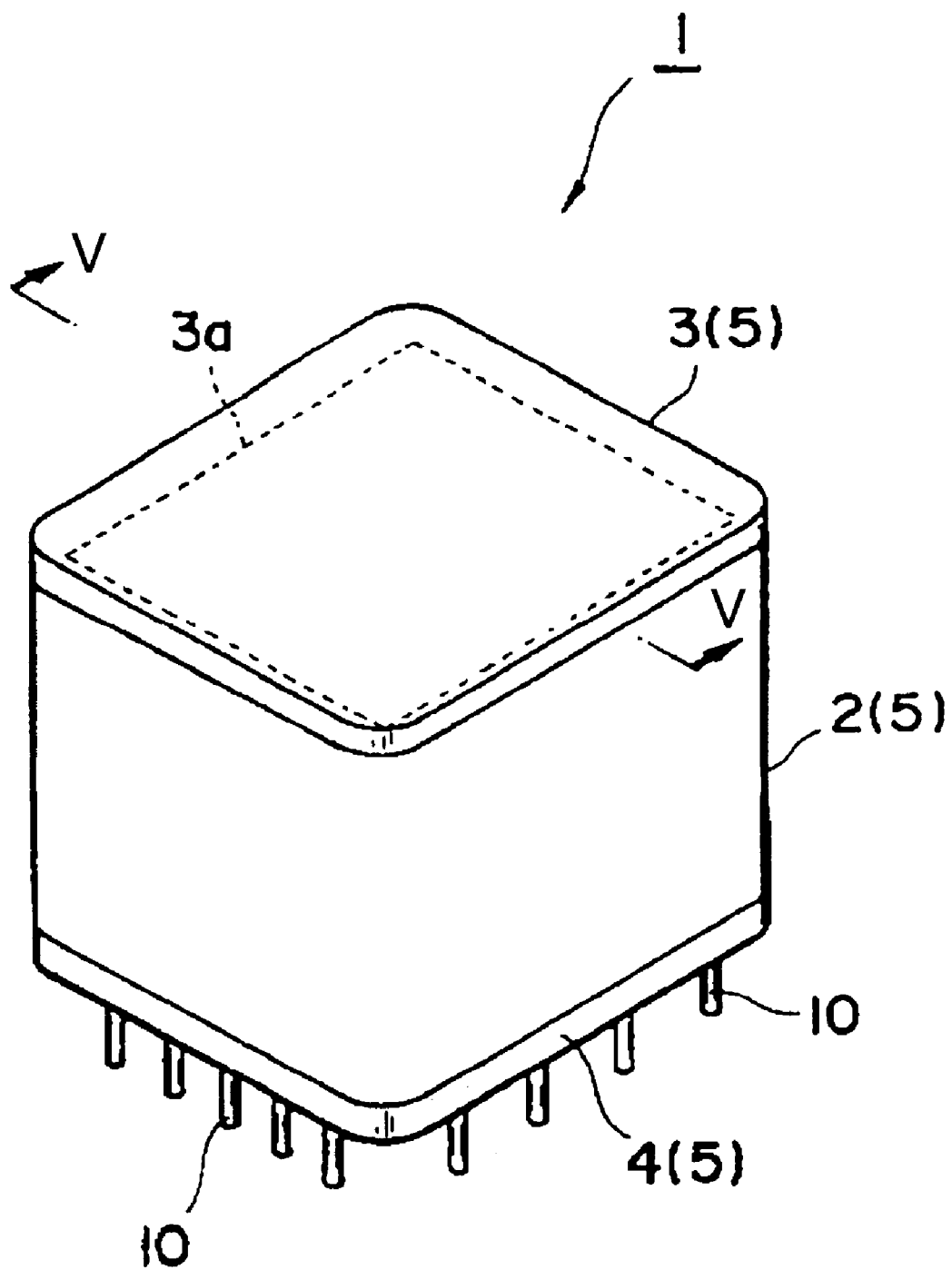
FIG. 4 is a perspective view showing the photomultiplier tube according to a first embodiment, which is used in a photomultiplier tube unit according to the present invention.
Figure 5:
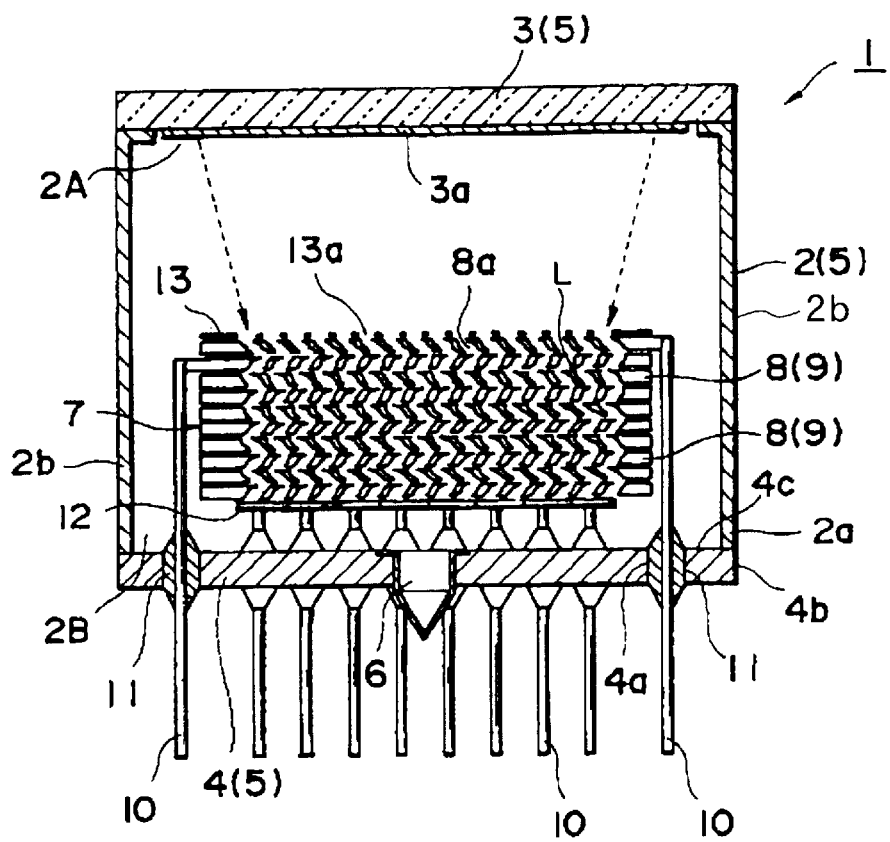
FIG. 5 is a cross-sectional view of the photomultiplier tube along the plane indicated by the arrows V in FIG. 4.

As shown in FIGS. 4 and 5, the photomultiplier tube 1 used in the unit A includes a side tube 2 formed of a metallic material such as Kovar metal or stainless steel and shaped substantially like an angular cylinder and having an open end 2A on one end and an open end 2B on the other; a faceplate 3 formed of glass material that is fused to the open end 2A; and a stem plate 4 formed of a metal (such as Kovar metal or stainless steel) is fused to the open end 2B. A photocathode 3a is formed on the inner surface of the faceplate 3 for converting light into electrons. The photocathode 3a is formed by causing alkaline metal vapor to react to antimony that has been pre-deposited on the faceplate 3. Here, the side tube 2, faceplate 3, and stem plate 4 are the components that construct an airtight vessel 5.

A metal exhaust tube 6 is fixed in the center of the stem plate 4. After operations for assembling the photomultiplier tube 1 are completed, the exhaust tube 6 is used to evacuate the vessel 5 using a vacuum pump (not shown) and to introduce an alkaline metal vapor into the vessel 5 when forming the photocathode 3a.

A block-shaped layered electron multiplier 7 is disposed inside the vessel 5. The electron multiplier 7 includes a ten-stage electron multiplying section 9 that has ten plate-shaped dynodes 8 constructed in layers. The electron multiplier 7 is supported in the vessel 5 by a plurality of stem pins 10 formed of Kovar metal. The stem pins 10 penetrate the stem plate 4. Internal ends of each stem pin 10 connect electrically to each dynode 8. Pinholes 4a are formed in the stem plate 4 to allow each stem pin 10 to pass through. A tablet 11 made of Kovar glass fills each pinhole 4a to form a hermetic seal between each stem pin 10 and the stem plate 4. Each stem pin 10 is fixed to the stem plate 4 via the tablet 11. The stem pins 10 are arranged in a ring around the stem plate 4 near an edge surface 4b of the stem plate 4.

An insulation substrate (not shown) is disposed in the electron multiplier 7 at a position below the electron multiplying section 9. Anodes 12 are juxtaposed on top of this insulation substrate. A flat focusing electrode plate 13 is disposed on the top layer of the electron multiplier 7 between the photocathode 3a and the electron multiplying section 9 and is formed with a plurality of slits 13a that are arranged linearly in the same direction. Each dynode 8 in the electron multiplying section 9 is also formed with a plurality of slits 8a having the same number as the slits 13a and also arranged linearly in a single direction.

Each electron multiplying path L that is formed by the slits 8a and pass through all layers of the dynodes 8 is given a one-on-one correspondence to each slit 13a in the focusing electrode plate 13, thereby forming a plurality of linear channels in the electron multiplier 7. Each anode 12 that is provided in the electron multiplier 7 has a one-on-one correspondence to each channel. By connecting each anode 12 to each stem pin 10, it is possible to extract discrete output from the vessel 5 via each stem pin 10.

In this way, linear channels are formed in the electron multiplier 7. A prescribed voltage is supplied to the electron multiplying section 9 and the anode 12 by connecting the stem pins 10 to a bleeder circuit. The photocathode 3a and focusing electrode plate 13 are set to the same potential, while the dynodes 8 and anode 12 are set to increasingly higher potentials beginning from the top stage. Light striking the faceplate 3 is converted to electrons by the photocathode 3a. The electrons enter prescribed channels by the electron lens effect of the focusing electrode plate 13. While passing through the electron multiplying path L of the dynodes 8, the electrons multiply at each stage of the dynodes 8, impinging on the anode 12. As a result, the output from each channel can be obtained from each anode.

Figure 6:
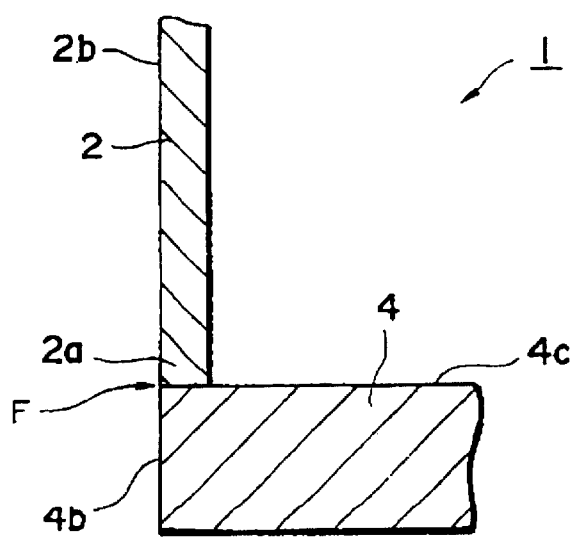
FIG. 6(a) is an enlarged cross-sectional view of the relevant part in FIG. 5 for describing a first example of hermetically welding a metal side tube to a metal stem plate.
FIG. 6(b) is an enlarged cross-sectional view of the relevant part in FIG. 5 for describing a second example of hermetically welding a metal side tube to a metal stem plate.
FIG. 6(c) is an enlarged cross-sectional view of the relevant part in FIG. 5 for describing a third example of hermetically welding a metal side tube to a metal stem plate.
FIG. 6(d) is an enlarged cross-sectional view of the relevant part in FIG. 5 for describing a fourth example of hermetically welding a metal side tube to a metal stem plate.
FIG. 6(e) is an enlarged cross-sectional view of the relevant part in FIG. 5 for describing a fifth example of hermetically welding a metal side tube to a metal stem plate.
FIG. 6(f) is an enlarged cross-sectional view of the relevant part in FIG. 5 for describing a sixth example of hermetically welding a metal side tube to a metal stem plate.
FIG. 6(g) is an enlarged cross-sectional view of the relevant part in FIG. 5 for describing a seventh example of hermetically welding a metal side tube to a metal stem plate.
FIG. 6(h) is an enlarged cross-sectional view of the relevant part in FIG. 5 for describing an eighth example of hermetically welding a metal side tube to a metal stem plate.
FIG. 6(i) is an enlarged cross-sectional view of the relevant part in FIG. 5 for describing a ninth example of hermetically welding a metal side tube to a metal stem plate.
Figure 6:
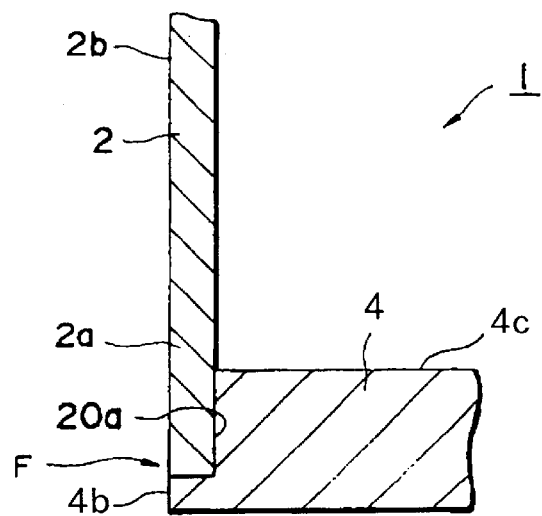
Figure 6:
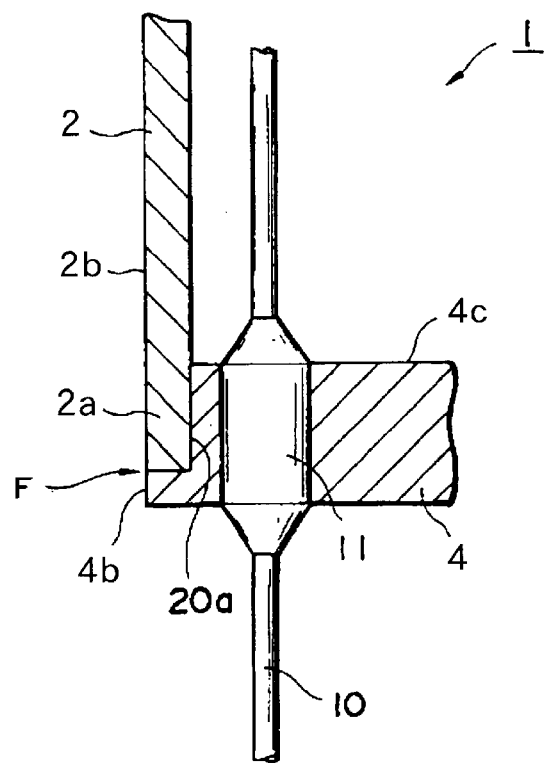
Figure 6:
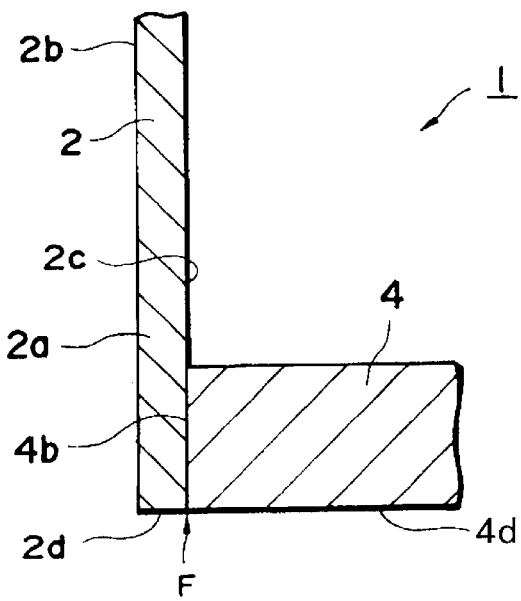
Figure 6:
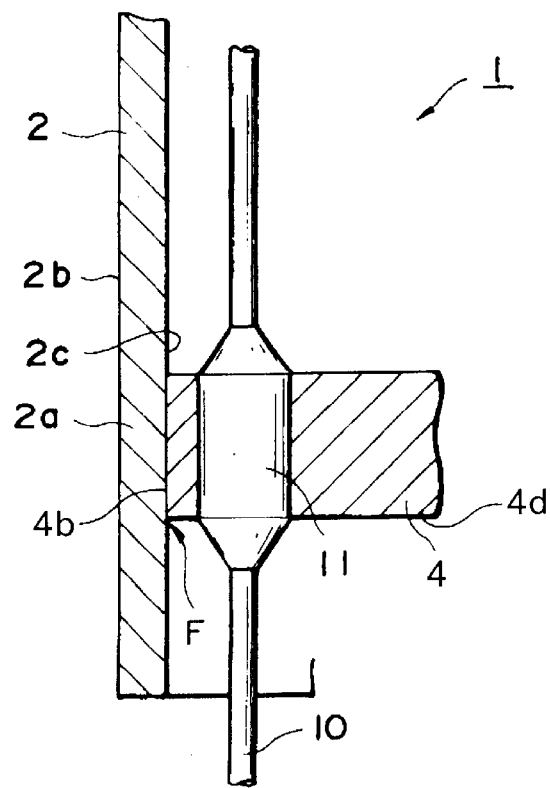
Figure 6:
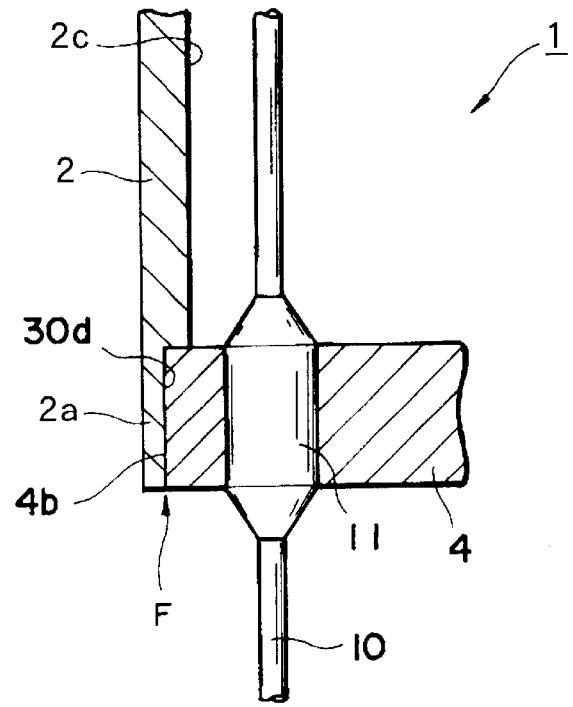
Figure 6:
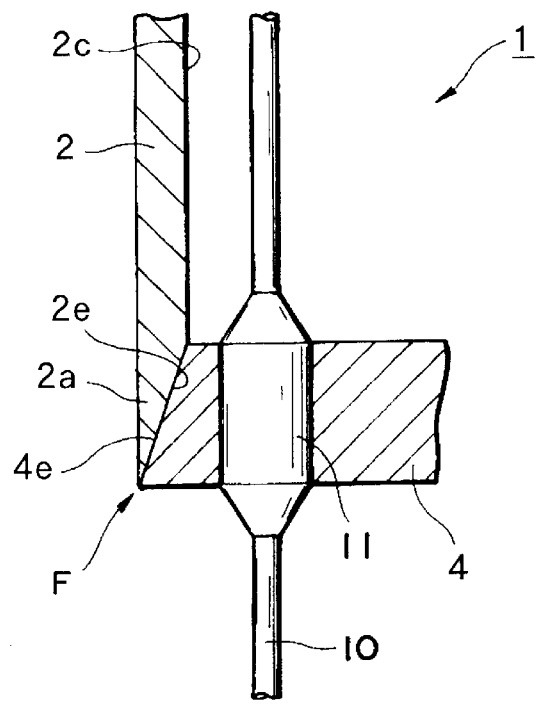
Figure 6:
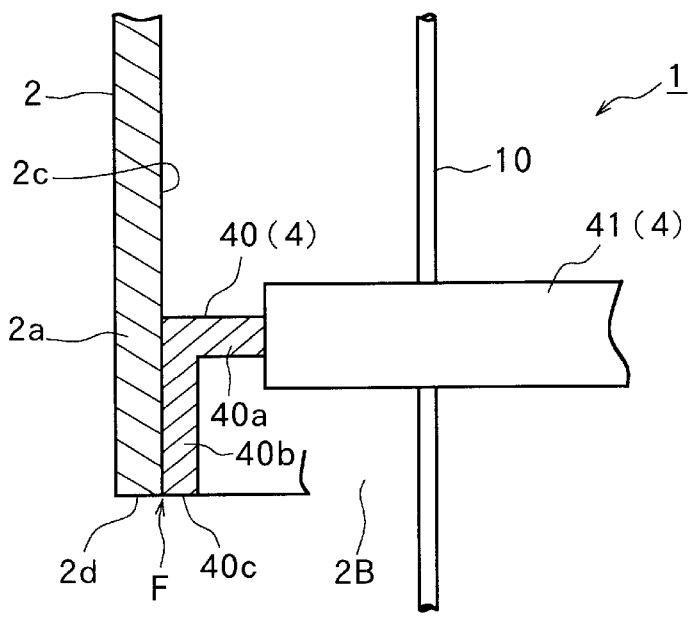
Figure 6:
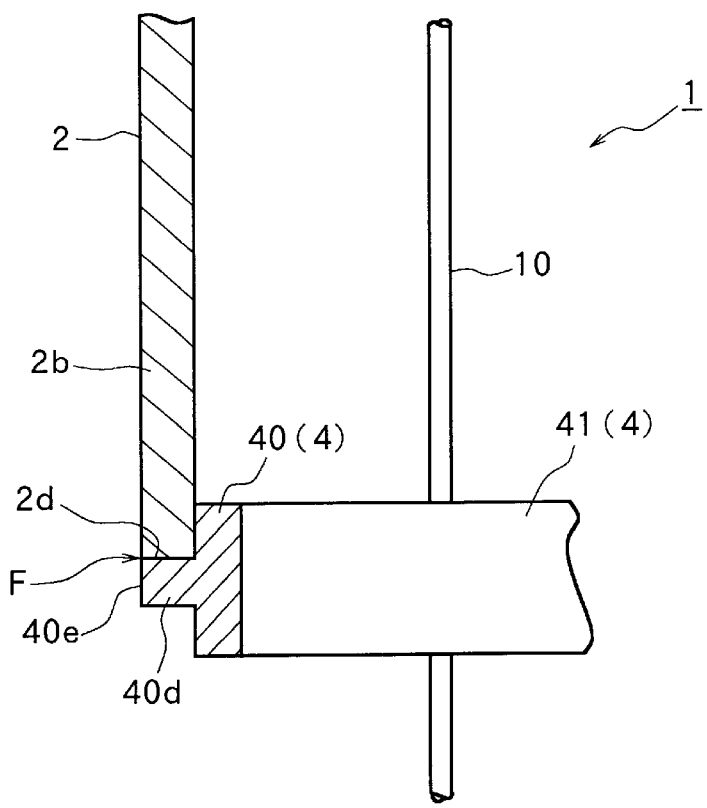
Figure 7:
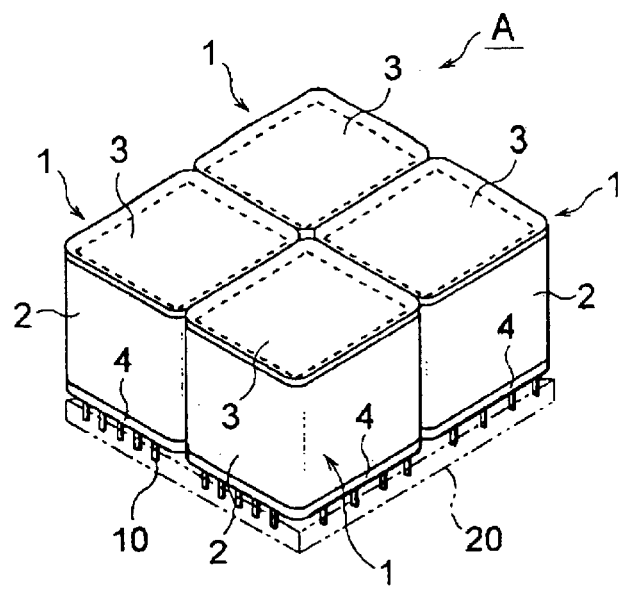
FIG. 7 is a perspective view showing a photomultiplier tube unit according to a first embodiment of the present invention.
Figure 8:
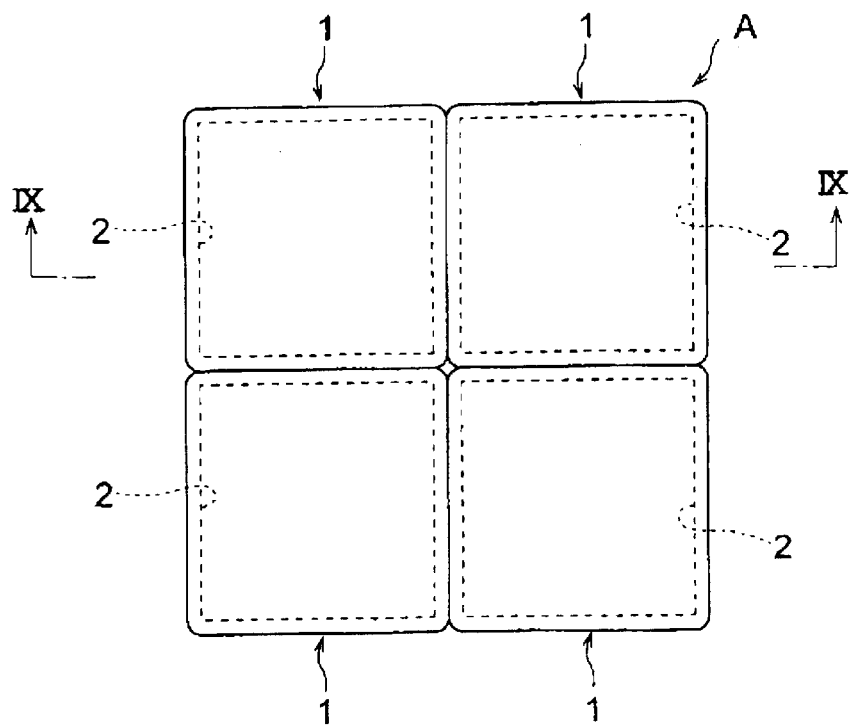
FIG. 8 is a plan view of the unit shown in FIG. 7.

FIG. 6(a) shows a first example of hermetically welding a metal side tube 2 to a metal stem plate 4. In this example, a bottom end 2a of the side tube 2 extending substantially in the axial direction of the tube is placed in contact with a top surface 4c of the stem plate 4, such that an outer surface 2b of the side tube 2 is flush with the edge surface 4b of the stem plate 4 along the axial direction. This construction eliminates protrusions such as a flange at the bottom of the photomultiplier tube 1. Referring to the point at which the bottom end 2a contacts the top surface 4c as a junction F, a laser beam external to the vessel 5 is irradiated directly horizontal or at a prescribed angle to the junction F, welding the two components together. In this way, the flange-like protrusions on the bottom of the photomultiplier tube 1 is eliminated. While posing difficulties for resistance welding, this construction allows the external dimensions of the photomultiplier tube to be reduced, helps to eliminate as much dead space as possible, and enables the side tubes to be positioned adjacent one another when juxtaposing a plurality of photomultiplier tubes. Accordingly, employing a laser welding to join the metal stem plate and side tube enables the photomultiplier tubes to be compact and to be more densely packed together. Another examples for hermetically welding a metal side tube 2 to a metal stem plate 4 will be described. In the following description, the same or like parts and components as those in the first example are designated by the same reference numerals to avoid duplicating description.

FIG. 6(b) shows a second example of hermetically welding a metal side tube 2 to a metal stem plate 4.

A photomultiplier tube has the metal stem plate 4. A cutout portion 20a is formed in the outer edge of the top surface 4c and has a step shape for placing the bottom end 2a of the side tube 2. The cutout portion 20a is formed in the top surface 4c around the entire edge of the stem plate 4 and has a rectangular ring shape that conforms to the shape of the side tube 2. The bottom end of the side tube 2 fits into the cutout portion 20a. The outer surface 2b is flush in the axial direction with the edge surface 4b.

By employing the fitting construction of the side tube 2 described above, the side tube 2 can be placed stably on the stem plate 4 before welding the junction F. Further, this construction facilitates positioning the side tube 2 over the stem plate 4. Moreover, after the junction F is welded, the reinforced construction can oppose a force toward the inside of the vessel 5A attempting to bend the side tube 2.

A laser beam external to the vessel 5A is irradiated directly horizontal to the junction F and/or at a prescribed angle to weld the components together. It is also possible to weld the junction F with an electron beam instead of the laser beam. In either case, the beams will not enter the vessel 5A during the welding process. Hence, the effects of heat on the internal parts can be avoided, as the formation of the side tube 2 prevents the beam from entering.

FIG. 6(c) shows a third example of hermetically welding a metal side tube 2 to a metal stem plate 4.

In the photomultiplier tube shown in FIG. 6(b), laser welding is employed to fuse the side tube 2 and stem plate 4 together, decreasing the amount of heat generated at the junction F. As a result, the stem pins 10 can be disposed near the side tube 2, as shown in FIG. 6(c), when the bottom end 2a is fit into the cutout portion 20a, such that the outer surface 2b and edge surface 4b are flush. This construction substantially prevents the effects of heat from generating cracks in the glass tablet 11 fixing the stem pins 10 to the stem plate 4. Accordingly, the stem pins 10 can be placed closer to the side tube 2, enabling the dynodes 8 to be expanded laterally. Such expansion increases the number of channels that can be formed in the electron multiplying section 9, providing a larger effective area in the electron multiplying section 9. By increasing the effective surface area in the electron multiplying section 9, it is possible to position the electron multiplying section 9 closer to the photocathode 3a, since the photoelectrons emitted from the photocathode 3a toward the focusing electrode plate 13 do not move at a large angle. This construction enables the height dimension of the vessel 5B to be reduced, thereby forming a compact photomultiplier tube having a larger effective surface area.

With conventional resistance welding, a distance of approximately 3.5 mm must be formed between the edge of the stem plate 4 and the center of the stem pins 10. Using laser beam or electron beam welding, however, it has been confirmed that a distance of 1.1 mm is sufficient. While the distance from the photocathode 3a to the focusing electrode plate 13 in the photomultiplier tube 1 of FIG. 6(b) is 7 mm, the lateral expansion of the electron multiplying section 9 in the photomultiplier tube 1 of FIG. 6(c) enables this distance to be reduced to 2.5 mm. By employing the laser beam or electron beam welding method, it is not only possible to eliminate the flange from the photomultiplier tube, but also to reduce the height dimension, thereby making great advances toward producing a compact photomultiplier tube.

When densely juxtaposing a plurality of photomultiplier tubes, the existence of a flange on the outside of the photomultiplier tubes has a great effect on this arrangement, particularly as the external dimensions decrease. For example, if an angular side tube 2 has external side dimensions of 25 mm and if the flange used for resistance welding has a width of 2 mm and protrudes externally around the entire edge of the tube, the flange portion occupies nearly 20 percent of the dimensions of the tube. Arranging this type of photomultiplier tube in a dense formation would generate a large proportion of dead space.

FIG. 6(d) shows a fourth example of hermetically welding a metal side tube 2 to a metal stem plate 4.

When forming an airtight weld between the stem plate 4 and side tube 2 shown in FIG. 6(d), the stem plate 4 is inserted into the open end 2B of the side tube 2, such that an inner surface 2c on the bottom end 2a contacts the edge surface 4b. At this time, a bottom surface 4d of the stem plate 4 is flush with a bottom end surface 2d of the side tube 2 in order that the bottom end surface 2d does not protrude lower than the stem plate 4. Accordingly, the outer surface 2b along the bottom end 2a extends substantially in the axial direction, and the flange protrusion is eliminated from the bottom end of the photomultiplier tube 1. When welding the junction F, a laser beam external to the photomultiplier tube 1 is radiated from directly beneath the junction F. Eliminating a flange-like protrusion from the bottom of the photomultiplier tube 1 poses difficulties for resistance welding. However, this construction allows the external dimensions of the photomultiplier tube 1 to be reduced and helps to eliminate as much dead space as possible when juxtaposing a plurality of photomultiplier tube 1, by enabling the side tubes 2 to be positioned close to one another. Accordingly, employing a laser welding method to join the stem plate 4 and side tube 2 can help reduce the size of the photomultiplier tube 1 and enables such photomultiplier tube 1 to be more densely packed together.

FIG. 6(e) shows a fifth example of hermetically welding a metal side tube 2 to a metal stem plate 4.

As shown in FIG. 6(e), a photomultiplier tube 1 is formed such that the bottom end 2a has a free end extending in the axial direction. Hence, the stem plate 4 is inserted through the open end 2B, such that the edge surface 4b contacts and slides inwardly on the inner surface 2c of the bottom end 2a. With this configuration, the distance between the top layer of the dynodes 8 in the electron multiplying section 9, which is fixed to the stem plate 4, and the photocathode 3a can easily be adjusted before the welding process to suit the need. This is performed simply by pushing on the bottom surface 4d of the stem plate 4 toward the inside of the side tube 2. Although the side tube 2 in the photomultiplier tube 1 of the present example extends in the axial direction of the tube, the side tube 2 can also be formed such that the open end 2B is wider than the open end 2A to facilitate insertion of the stem plate 4 into the photomultiplier tube 1.

When employing laser welding to weld the junction F, it is possible to decrease the heat generated at the junction F. Hence, as described in the third example shown in FIG. 6(c), the stem pins 10 can be positioned closer to the side tube 2, thereby producing a more compact photomultiplier tube of the same size described in the third example.

FIG. 6(f) shows a sixth example of hermetically welding a metal side tube 2 to a metal stem plate 4.

In a photomultiplier tube 1 of the sixth example, as shown in FIG. 6(f), a cutout portion 30d having a cross section shaped as the letter L is formed in the inner surface 2c. The cutout portion 30d enables the outer edge of the stem plate 4 to be inserted therein. The cutout portion 30d forms a rectangular ring around the entire inner surface 2c and conforms to the outer shape of the stem plate 4. By employing this construction, it is possible to rest the side tube 2 stably on the stem plate 4 before welding the junction F, thereby easily positioning the side tube 2 in relation to the stem plate 4. Moreover, the interval between the top layer of the dynodes 8 in the electron multiplying section 9, which is fixed to the stem plate 4, and the photocathode 3a formed on the faceplate 3 can be easily set by adjusting the depth of the cutout portion 30d.

The junction F is welded by irradiating a laser beam thereon. It is also possible to use an electron beam in place of the laser beam. In either case, the beam does not enter the evacuated vessel during the welding process, thereby avoiding heat affecting the internal components, since the cutout portion 30d blocks the penetration of such beams.

FIG. 6(g) shows a seventh example of hermetically welding a metal side tube 2 to a metal stem plate 4.

In a photomultiplier tube 1 of the seventh example, as shown in FIG. 6(g), a tapered surface 2e is formed in the inner surface 2c of the bottom end 2a and a tapered edged surface 4e is formed in the stem plate 4. The tapered surface 2e forms a rectangular ring around the entire inner surface 2c and conforms to the tapered edged surface 4e of the stem plate 4. By employing this construction, it is possible to rest the side tube 2 stably on the stem plate 4 before welding the junction F, thereby easily positioning the side tube 2 in relation to the stem plate 4.

FIG. 6(h) shows an eighth example of hermetically welding a metal side tube 2 to a metal stem plate 4.

A photomultiplier tube 1 of the eighth embodiment includes a metal stem support member 40 that contacts the inner surface 2c of the bottom end 2a; and a glass stem plate 41 that is square-shaped and planar and supported by this stem support member 40. The stem support member 40 has a cross-section substantially shaped like the letter L having a horizontal portion 40a and a vertical portion 40b. The horizontal portion 40a is fixed to each side surface of the stem plate 41. The vertical portion 40b extends in the axial direction of the tube while contacting the inner surface 2c. A bottom end surface 40c of the vertical portion 40b is flush with the outer surface 2b. The stem pins 10 penetrate the stem plate 41. In the first to seventh examples, the tablets 11 formed of Kovar glass fill each pinhole 4a through which the stem pins 10 penetrate, in order to maintain insulation between the stem pins 10 and the metal stem plate 4. In the present example, however, the tablets 11 are unnecessary because the stem pins 10 penetrate a glass stem plate 41, which is formed of glass.

In order to manufacture the photomultiplier tube 1 of the present example, the stem support member 40 is pre-fixed to all sides of the stem plate 41, thereby forming the stem plate 4. The stem plate 4 is inserted into the side tube 2 through the open end 2B, sliding the edge surface 4b in contact with the inner surface 2c. The stem plate 4 is slid into the side tube 2 until the bottom end surface 40c is flush with the bottom end surface 2d. The junction F is welded by a laser.

In the present example, the interval between the top layer of the dynodes 8 in the electron multiplying section 9, which is fixed to the stem plate 4, and the photocathode 3a formed on the faceplate 3 can be regulated by adjusting the length of the vertical portion 40b.

FIG. 6(i) shows a ninth example of hermetically welding a metal side tube 2 to a metal stem plate 4.

Similar to the eighth example shown in FIG. 6(h), a photomultiplier tube 1 shown in FIG. 6(i) includes the stem plate 4 configured of the stem support member 40 and the stem plate 41, wherein the stem plate 4 is welded to the bottom end 2a to form an airtight seal. The stem support member 40 has a cross section shaped substantially like the letter T. The top surface of a horizontal protrusion 40d of the stem support member 40 contacts the bottom end surface 2d of the side tube 2, such that an edge surface 40e of the horizontal protrusion 40d is flush with the outer surface 2b in the axial direction of the side tube 2.

The horizontal protrusion 4d of the stem support member 40 is preprocessed to have a protruding length equivalent to the thickness of the side tube 2. With this configuration, it is possible to mount the side tube 2 stably on the stem plate 4 prior to laser welding the junction F, facilitating the positioning of the side tube 2.

The photomultiplier tubes in all the examples described above are constructed without a flange-like protrusion. As a result, it is difficult to join the stem plate 4 and side tube 2 using the resistance welding method that is employed in the conventional method. However, the junction can be joined through laser welding. As a result, the present invention can reduce the dimensions of the photomultiplier tube, thereby eliminating as much dead space as possible when a plurality of photomultiplier tubes are arranged together, enabling the side tubs 2 to be disposed near one another. Hence, the use of laser welding to join the stem plate 4 and side tube 2 can reduce the size of the photomultiplier tube and enable more densely packed arrays.

Further, the use of a laser for welding the side tube 2 to the stem plate 4 differs from resistance welding by eliminating the need to apply pressure on the side tube 2 and the stem plate 4 at the junction F. Accordingly, residual stress is not generated at the junction F. This makes it unlikely for cracking to occur during use at the junctions and greatly helps improve the durability of the apparatus and strengthens the hermetic seal.

In the examples described above, laser welding was used as the example for welding the side tube 2 and the stem plate 4 together. However, it is also possible to use an electron beam in place of the laser beam. Since both laser beam and electron beam welding can reduce the amount of heat generated at the junction F compared to that generated during resistance welding, the effects of heat on components mounted in the vessel 5 is extremely small when assembling the photomultiplier tube.

In forming the unit A using the photomultiplier tubes 1 described above, the photomultiplier tubes 1 with the same configuration are arranged to be a 2 lines by 2 columns formation on a substrate 20 made from resin or ceramics. This can be done by contacting the outer surfaces 2b of the side tubes 2 which are in the form of a rectangular cylinder wherein each outer surface is perpendicular in entirety to the corresponding photocathode 3a. In this case, connection of the opposing side tubes 2 can be accomplished easily and firmly while assuring electrical conductivity between the side tubes when an electrically conductive adhesive is used for connection. Electrically connecting the side tubes of the photomultiplier tubes 1 renders the connected side tubes be in the same potential, so that electrical connections between the stem pins and the side tube 2 in each photomultiplier tube are unnecessary. Thus, the unit assembling is easy to perform.

Figure 9:
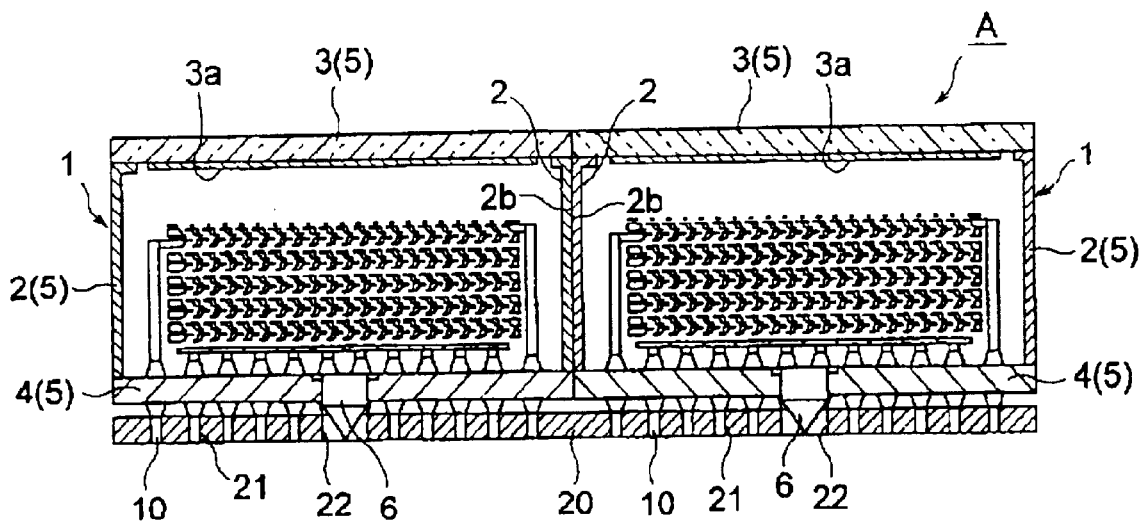
FIG. 9 is a cross-sectional view of the photomultiplier tube unit along the plane indicated by the arrows IX in FIG. 8.
Figure 10:
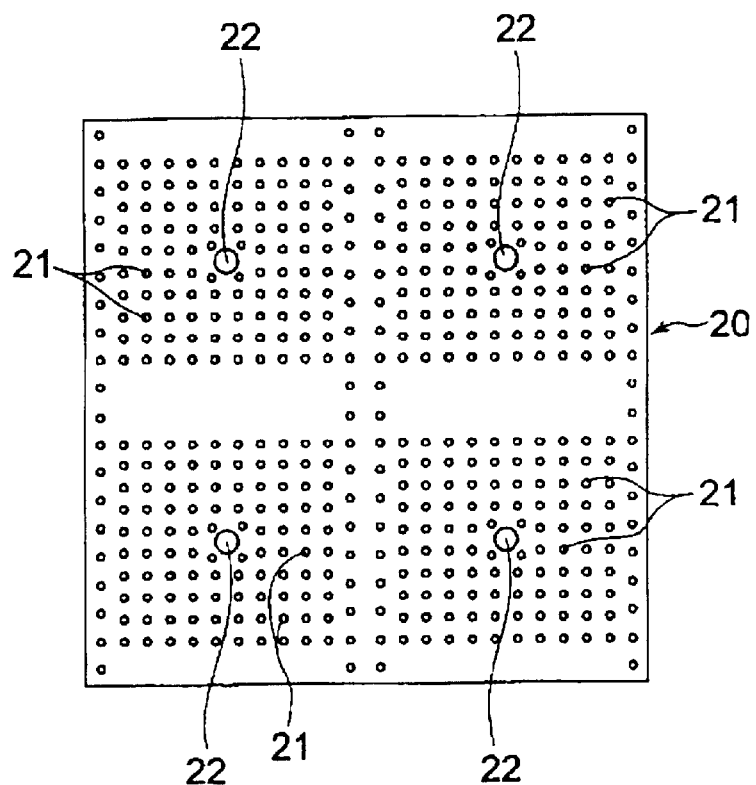
FIG. 10 is a plan view showing a substrate shown in FIG. 9.
Figure 11:
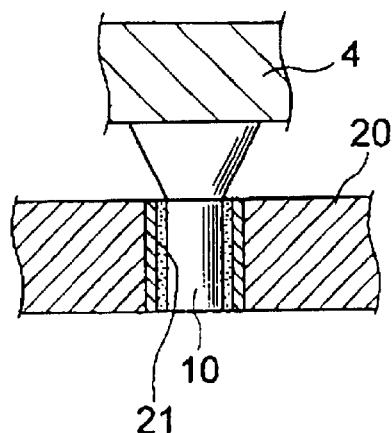
FIG. 11 is an enlarged cross-sectional view showing a stem pin inserted and fixed in a pin hole on the substrate.

As shown in FIGS. 9 and 10, a number of pin holes 21 are formed in the substrate 20 to form a pattern corresponding to the arrangement of the stem pins 10 of the photomultiplier tube 1. The substrate 20 is further formed with four exhaust pipe insertion holes 22 for allowing respective exhaust pipes 6 of four photomultiplier tubes 1 to be inserted therein. The pin holes 21 for each photomultiplier tube 1 are arranged around the exhaust pipe insertion hole 22. By inserting the stem pins 10 into the pin holes 21 in the substrate 20 (see FIG. 11) and also inserting the exhaust pipes 6 into the exhaust pipe insertion holes 22, alignment of the photomultiplier tubes 1 on the substrate 1 can be done easily. In the case where a circuit board is mounted on the substrate 20, soldering is used to fix the stem pins 10 in the pin holes 21. An adhesive is also available for fixing the stem pins 10 in the pin holes 21.

The units B and C in which the photomultiplier tubes are cascade-connected as shown in FIG. 3 are similar in configuration to the unit A. Difference resides only in the arrangement pattern and the number of the photomultiplier tubes 1. Hence, further description of units B and C is omitted herein. It would be apparent that the number and the arrangement pattern of the photomultiplier tubes 1 forming each unit are variable depending on the circumstance in which the photomultiplier tubes 1 are used.

Because the outer surfaces 2b of the metal side tubes 2 in one unit are in facial contact with one another wherein each outer surface is perpendicular in entirety to the corresponding photocathode 3a, a high-density arrangement of the photomultiplier tubes 1 can be achieved. Furthermore, with the unit of the photomultiplier tubes, when one of a plurality of photomultiplier tubes 1 forming a radiation detector 40 (e.g., a gamma camera) is to be replaced with a new one, such a complicated procedure as to replace the photomultiplier tubes one by one is not needed but a replacing procedure can be accomplished simply and easily. The photomultiplier tubes 1 are arranged on the substrate 20 so that not only is easy to align the photomultiplier tubes 1 but also is improved the alignment accuracy. Moreover, the management of the number and the arrangement of the photomultiplier tubes 1 in one unit can be performed depending on the shape of the substrate 20, so the maintenance and the management on a unit basis can be easily done.

Figure 12:
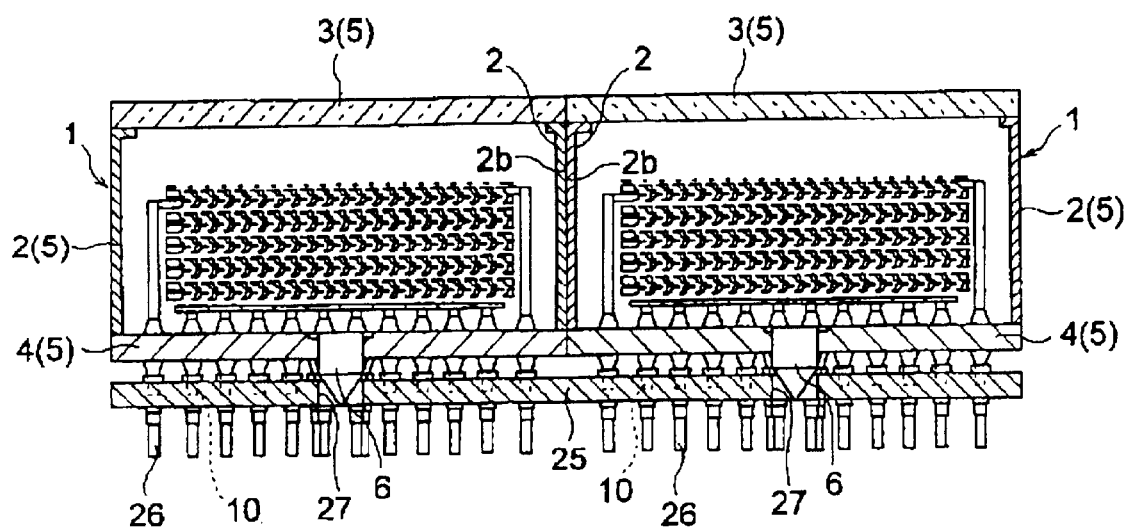
FIG. 12 a view showing a photomultiplier tube unit according to a second embodiment of the present invention.
Figure 13:
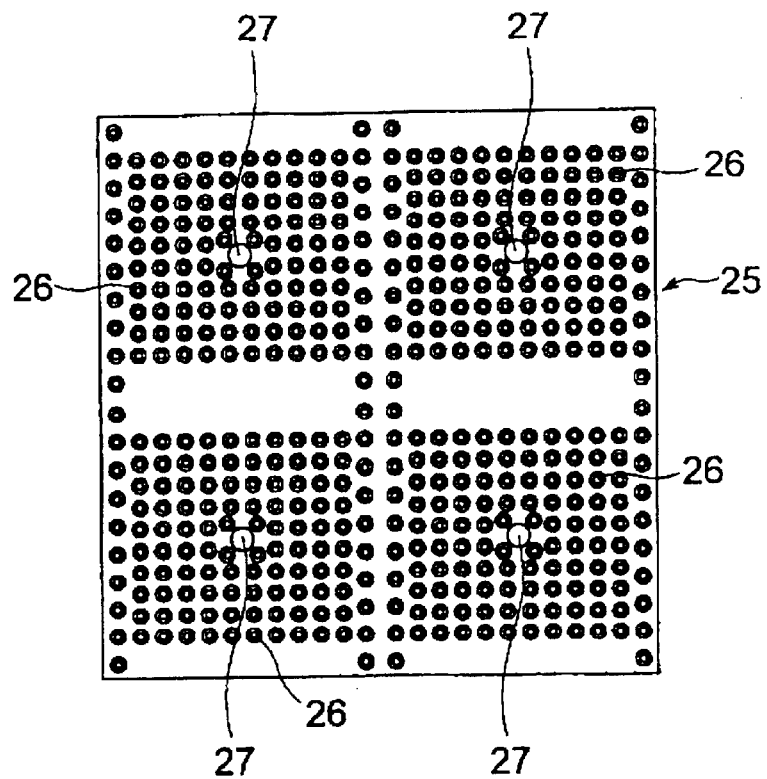
FIG. 13 a plan view showing a substrate shown in FIG. 12.
Figure 14:
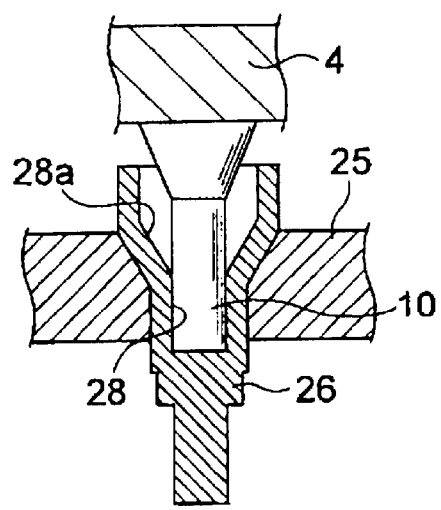
FIG. 14 is an enlarged cross-sectional view showing a stem pin inserted and fixed in a pin hole on the substrate.

The photomultiplier tube unit according to the present invention is not limited to the above-described embodiments. For example, as shown in FIGS. 12 and 13, socket pins 26 are fixed to the substrate 25, which are arranged in a pattern corresponding to the pattern in which the stem pins 10 are arranged. The substrate 25 is formed with four exhaust tube insertion holes 27 for inserting the exhaust tubes 6 of the photomultiplier tubes 1. The socket pins 26 are arranged to surround each exhaust tube insertion hole 27. As shown in FIG. 14, the lower end of the socket pin 26 projects from the substrate 25. The upper portion of the socket pin 26 is formed with a concave portion 28 for receiving the stem pin 10. The upper portion of the concave portion 28 is formed with a conical guide portion 28a to ease insertion of the stem pin 10 in the concave portion 28. The stem pins 10 are inserted into the respective concave portions 28 of the socket pins 26 (see FIG. 14) and the exhaust pipes 6 are inserted into the respective exhaust pipe insertion holes 27, thereby aligning the photomultiplier tubes 1 on the substrate 25.

Figure 15:
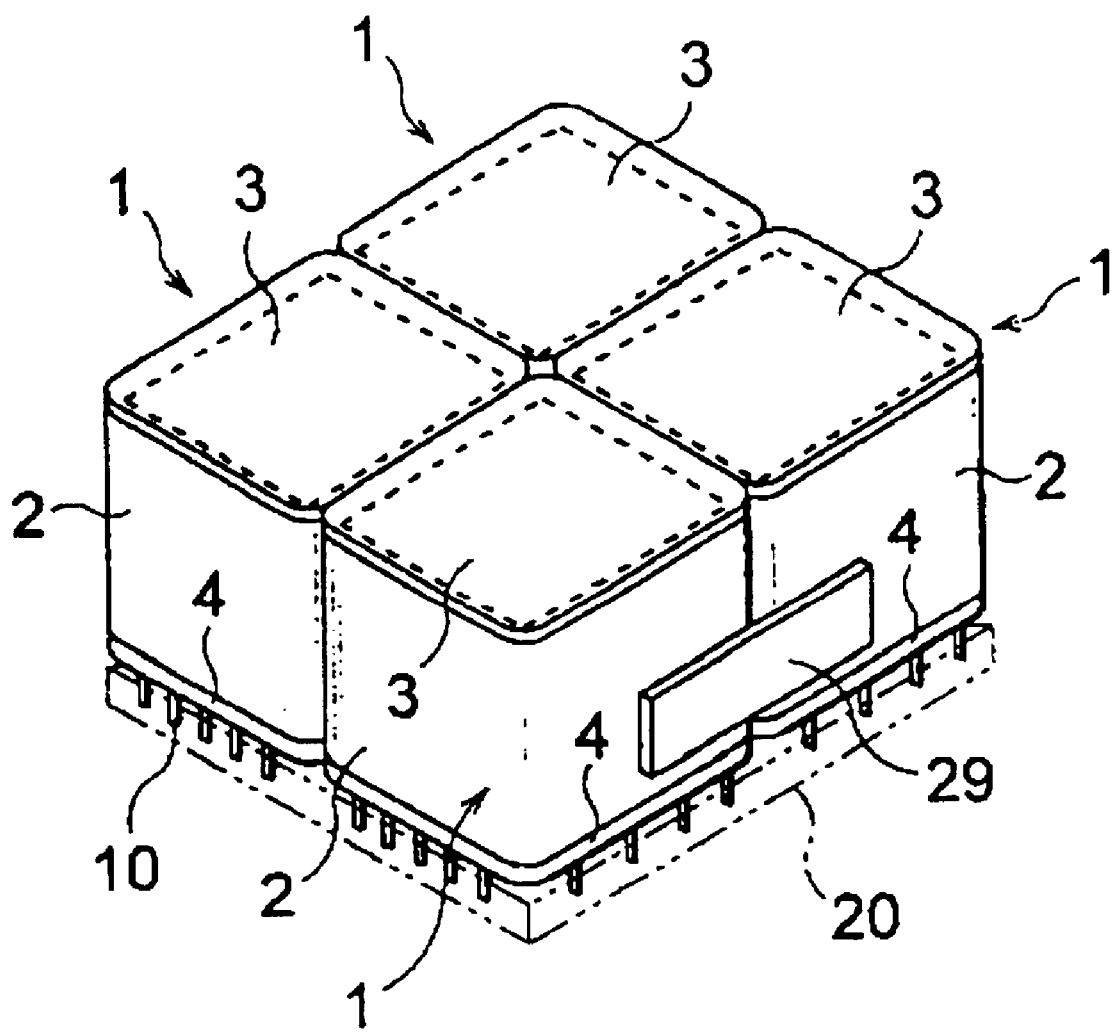
FIG. 15 is a perspective view showing a photomultiplier tube unit according to a third embodiment of the present invention.

As a further embodiment of the unit, the side tubes 2 may be connected using an electrically conductive plate 26 while placing the photomultiplier tubes 1 in a condition that the outer surfaces 2b of the side tubes 2 are in facial contact with one another as shown in FIG. 15 wherein each outer surface is perpendicular in entirety to the corresponding photocathode 3a. With such a structure, electrical connection between the side tubes 2 of the photomultiplier tubes 1 is ensured and it is easy to maintain the side tubes 2 that are connected at the same potential.

What is claimed is:

1. A photomultiplier tube unit comprising:
   a plurality of photomultiplier tubes that are juxtaposed, each of the plurality of photomultiplier tube including:
      a faceplate;
      a photocathode for emitting electrons in response to light incident on the faceplate;
      an airtight vessel;
      an electron multiplying section, disposed inside the airtight vessel, for multiplying the electrons emitted from the photocathode; and
      an anode for outputting an output signal based on the electrons multiplied by the electron multiplying section,
   wherein the airtight vessel comprises:
      a metal stem plate for fixedly supporting the electron multiplying section and the anode with stem pins; and
      a metal side tube with the stem plate fixed on one open end, and enclosing the electron multiplying section and the anode;
      wherein the faceplate is fixed on the other open end of the metal side tube,
      and wherein a plurality of airtight vessels are juxtaposed and outer surfaces of the plurality of airtight vessels are flat and in facial contact with one another, each outer surface being perpendicular in entirety to the corresponding photocathode.

2. The photomultiplier tube unit according to claim 1, wherein the plurality of airtight vessels are arranged and fixed on a single substrate.

3. The photomultiplier tube unit according to claim 2, wherein the substrate is formed with a plurality of pin holes for allowing the stem pins to be inserted therein.

4. The photomultiplier tube unit according to claim 2, wherein the substrate is provided with a plurality of socket pins having an upper portion formed with a concave portion for allowing the stem pin to be inserted therein.

5. The photomultiplier tube unit according to claim 1, wherein the outer surfaces of the side tubes are in facial contact with one another via an electrically conductive adhesive.

6. The photomultiplier tube unit according to claim 1, wherein the stem plate and the one end of the metal side tube are welded by a laser beam.

7. The photomultiplier tube unit according to claim 1, wherein the stem plate and the one end of the metal side tube are welded by an electron beam.

8. A radiation detector comprising:
   a scintillator for emitting fluorescent light in response to radiation generated from an object of analysis;
   a plurality of photomultiplier tubes for outputting electric charges based on fluorescent light emitted from the scintillator, and a position calculating section for performing calculations on the electric charges output from the plurality of photomultiplier tubes and outputting positioning signals of radiation issued from the object of analysis,
   wherein each of the plurality of the photomultiplier tubes comprises:
      a faceplate disposed in opposition to the scintillator;
      a photocathode for emitting electrons in response to light incident on the faceplate;
      an airtight vessel;
      an electron multiplying section, disposed inside the airtight vessel, for multiplying the electrons emitted from the photocathode; and an anode for outputting an output signal based on the electrons multiplied by the electron multiplying section, wherein the airtight vessel comprises:
  a metal stem plate for fixedly supporting the electron multiplying section and the anode with stem pins; and
  a metal side tube with the stem plate fixed on one open end, and enclosing the electron multiplying section and the anode;
  wherein the faceplate is fixed on the other open end of the metal side tube, and wherein the radiation detector includes a photomultiplier tube unit in which a plurality of airtight vessels are juxtaposed, and outer surfaces of the plurality of airtight vessels are flat and in facial contact with one another, each outer surface being perpendicular in entirety to the corresponding photocathode.

9. The radiation detector according to claim 5, wherein the plurality of airtight vessels of the photomultiplier tube unit are arranged and fixed on a single substrate.

* * * * *